US007691581B2

(12) United States Patent
Kintrup et al.

(10) Patent No.: US 7,691,581 B2
(45) Date of Patent: Apr. 6, 2010

(54) MEANS AND METHODS FOR DIAGNOSING A TREPONEMA INFECTION

(75) Inventors: Martin Kintrup, Gauting (DE); Heike Thüring-Nahler, Oberasbach (DE); Lilly Kronsteiner, Planegg (DE); Vera Helbl, München (DE); Heinz Engel, München (DE); Ludwig Furtmayr, Steingaden (DE)

(73) Assignee: Viramed Biotech AG, Planegg/Steinkirchen (DE)

( * ) Notice: Subject to any disclaimer, the term of this patent is extended or adjusted under 35 U.S.C. 154(b) by 166 days.

(21) Appl. No.: 10/533,618

(22) PCT Filed: Oct. 29, 2003

(86) PCT No.: PCT/EP03/12011

§ 371 (c)(1),
(2), (4) Date: Feb. 6, 2006

(87) PCT Pub. No.: WO2004/040311

PCT Pub. Date: May 13, 2005

(65) Prior Publication Data

US 2006/0171967 A1    Aug. 3, 2006

(30) Foreign Application Priority Data

Oct. 29, 2002  (DE) ................ 102 50 368

(51) Int. Cl.
*G01N 33/571* (2006.01)
(52) U.S. Cl. ........................................ 435/7.1
(58) Field of Classification Search ............ None
See application file for complete search history.

(56) References Cited

U.S. PATENT DOCUMENTS 3,564,089 A    2/1971    Kiddy

FOREIGN PATENT DOCUMENTS

| DE | 195 36 166 C1 | 3/1997 |
|---|---|---|
| DE | 694125 709 T2 | 3/2001 |
| WO | WO 91/10138 | 7/1991 |
| WO | WO97/13151 | 4/1997 |

OTHER PUBLICATIONS

West et al. (Sex. Transm. Infect., 78:282-285, Aug. 2002).*
Omega Diagnostics (Omega Diagnostics Ltd., IMMUTREP RPR product sheet).*
Becton, Dickinson, and Company (BD Macro-Vue RPR Card Tests).*
Egglestone et al. (Communicable Dis. Pub. Health, 3:158-162, 2000).*
Zarakolu et al. (J. Clin. Microbiol., 40:3064-6065, Aug. 2002).*
ASI RPR test card product insert.*
Weiner Labs RPR product insert.*
Krebs et al., "Lues, Seuche Und Serologie Syphilis Up-To-Date, Infection and Serology," *Schweiz. Rundschau Med. (PRAXIS)*, 71:1807-1811 (1982).
Larsen et al., "Laboratory Diagnosis and Interpretation of Tests for Syphilis," *Clin. Microbial. Rev.*, 8:1-21 (1995).
Lefevre et al., "Evaluation of the Captia Enzyme Immunoassays for Detection of Immunoglobulins G and M to *Treponema-pallidum* in Syphilis," *J. Clin. Microbial.*, 28:1704-1707 (1990).
Miranda et al., "A Comparison of VDRL and Immunoassays Developed with a Recombinant TmpA Antigen in the Screening of Antibodies to *Treponema pallidum*," *Serodiagnosis and Immunotherapy in Infectious Disease*, 8:149-155 (1997).
Pedersen et al., "Enzyme-Linked Immunosorbent Assay for Detection of Antibodies to the Venereal Disease Research Laboratory (VDRL) Antigen in Syphilis," J. Clin. Microbiol., 25:1711-1716 (1987).
Sambri et al., "Western Immunoblotting with Five *Treponema pallidum* Recombinant Antigens for Serologic Diagnosis of Syphilis," *Clinical and Diagnostic Laboratory Immunology*, 8:534-539 (2001).
Young et al., "A New Recombinant Antigen Latex Agglutination Test (Syphilis Fast) for the Rapid Serological Diagnosis of Syphilis." *Intl. J. of STD and AIDS*, 9:196-200 (1998).
Zrein etal., "Recombinant Antigen-Based Enzyme Immunoassay for Screening of *Treponema pallidum* Antibodies in Blood Bank Routine," *J. Clin. Microbiol.*, 33:525-527 (1995).
International Search Report, PCT/EP03/12011, European Searching Authority, dated Feb. 5, 2004.

\* cited by examiner

*Primary Examiner*—Robert B Mondesi
*Assistant Examiner*—Brian J Gangle
(74) *Attorney, Agent, or Firm*—Marshall, Gerstein & Borun LLP

(57) ABSTRACT

The present invention relates to a carrier for diagnostics and/or follow-up of a *Treponema* infection and to a diagnostic method using said carrier. According to the invention a carrier is provided for diagnostics and/or follow-up of a *Treponema* infection, said carrier comprising at least one immobilized cardiolipin and at least one immobilized *Treponema*-specific antigen. Furthermore, a method is provided for diagnostics and/or follow-up using the carrier.

34 Claims, 5 Drawing Sheets

Treponema+VDRL ViraBlot
Mother:
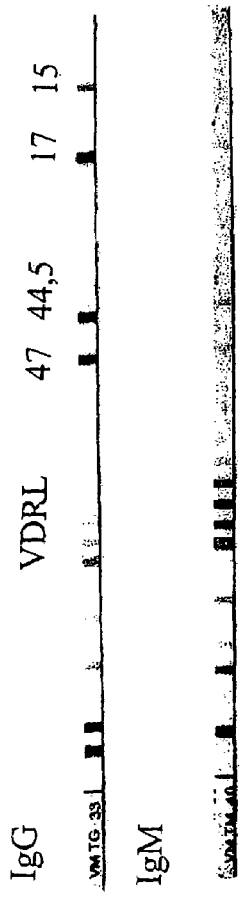
Child:
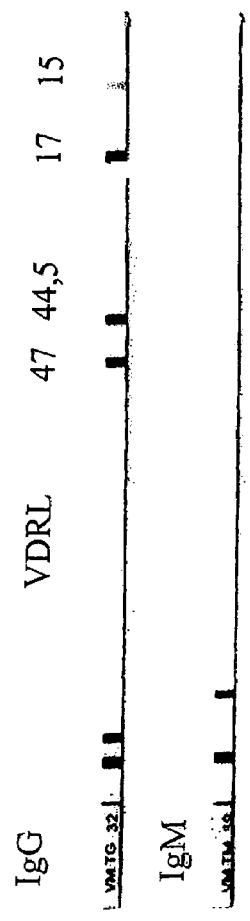
Results with conventional tests:
TPPA >1:20000
19S-IgM-FTA-ABS 1:160
Cardiolipin-KBR >1:160
TPPA 1:5120
IgG-FTA-ABS positive
19S-IgM-FTA-ABS negative
Cardiolipin-KBR 1:40
Fig. 5

MEANS AND METHODS FOR DIAGNOSING A TREPONEMA INFECTION

The present invention relates to a carrier for diagnostics and/or follow-up of a Treponema infection and to a diagnostic method using said carrier. *Treponema* infections can thereby be detected, confirmed and controlled in the course of the disease.

Basically, the course of syphilis may be in several stages, which are called primary syphilis, secondary syphilis and tertiary syphilis.

Direct pathogen detection only offers a good possibility of diagnosis in the primary stage. Detection is here directly carried out on the basis of the tissue sample and can be performed by dark-field microscopy, direct immunofluorescence or by a *Treponema pallidum*-specific PCR.

Serological methods for the detection of antibodies are easily possible in all stages of disease. They throw light on characteristic antibody constellations which furnish information on the need for therapy.

Anti-*Treponema pallidum* specific antibodies and antibodies against cardiolipin play an important role.

Anti-cardiolipin antibodies of the IgG or IgM type may occur in patients with *Treponema* infections and can be detected with the CMT test (cardiolipin microflocculation test, English VDRL test: Veneral Disease Research Laboratories Test) or the RPR test (Rapid Plasma Reagin Test) or the cardiolipin complement-binding reaction test. In these analytical methods positive signals are observed in the presence of anti-lipoidal antibodies in the sample. The VDRL test can be performed quantitatively with appropriate sample dilutions, so that a titer is assessed to be positive in which a distinct flocculation occurs. The test is well suited for follow-up and therapy control, but can also react unspecifically. Among other things, cross reactions arise in autoimmune diseases, e.g. in anti-phospholipid syndrome or in systemic lupus erythematosus.

Anti-*Treponema pallidum* specific antibodies can be formed against protein from *Treponema pallidum*. The detection of these antibodies can be performed as screening test, as TPHA (*Treponema pallidum* hemagglutination test), TPPA (*Treponema pallidum* particle agglutination test) or TPLA (*Treponema pallidum* latex agglutination test).

Among other things, the diagnostically relevant proteins deriving from *Treponema pallidum* comprise proteins with molecular weights of 47 kD, 44.5 kD, 37 kD, 17 kD and 15 kD (Labor und Diagnose, Editor: Lothar Thomas, pages 1234 et seq., TH-Books Verlagsgesellschaft mbH, Frankfurt/Main, 2000; DE19536166; WO8802403; Sambri et al., Clin. Diagn. Lab. Immunol. 2001 May; 8(3):534-9). In various standard tests (Innolia Syphilis, Innogenetics, Belgium; *Treponema* Marblot, MarDx, USA; *Treponema* Recomblot, Mikrogen, Germany) combinations of these proteins are immobilized on solid-phase carrier materials. During incubation of the sample with the coated carrier material *Treponema pallidum*-specific antibodies may bind to the antigens and are subsequently detected in an immunochemical reaction. The detection of these *Treponema pallidum*-specific antibodies can be used in terms of an ELISA (enzyme-linked immunosorbent assay), for instance as screening test for syphilis or in terms of immunoblots as confirmation test for syphilis.

Therefore immunoblots are used as confirmation tests and for follow-up in indistinct diagnostic findings obtained from the search reactions.

Primarily, to assess the need for therapy test methods for the determination of anti-*Treponema pallidum* specific IgM antibodies are of importance. Typically, this detection is possible with a Tp-IgM-FTA test (fluorescent *Treponema* antibody absorption test) or with a Tp-IgM-Elisa or with a *Treponema pallidum* IgM immunoblot.

In particular, methods which include at least a semi-quantitative detection of anti-cardiolipin antibodies are indicated for the serologic follow-up and therapy control.

In U.S. Pat. No. 3,564,089 the combination of Reiter treponemes and VDRL antigens is used in one test to detect the appropriate antibodies in a patient's material. By contrast, this detection of antibodies which are directed against antigens of Reiter treponemes is not suited for specifically detecting those antibodies that are directed against the real pathogen of syphilis (*Treponema pallidum*).

The test format of U.S. Pat. No. 3,564,089 allows no separate detection of the antibody reaction with the Reiter antigens or the VDRL antigens. Rather, the detected antibody reactivity is the sum of both reactivities. A separate detection of different antibody reactivities in the patient's material, e.g. on the one hand the reactivity with *Treponema*-specific antigens and on the other hand with the VDRL antigens, shows, however, advantages in diagnostics, as will be described later in detail.

Appropriate serologic confirmation detection methods known from the prior art do not allow any quantitative determination of antibodies in the patient's sample, nor any distinction between different reactivities in the analytical material. Furthermore, they have the disadvantage that they do virtually not allow any determination as to whether a *Treponema* infection is still acute or has already subsided. Among other things, this is due to the fact that antibodies against *Treponema* antigen are still detectable for a very long time even if the actual infection, i.e. the presence of pathogens, has already subsided. In addition, the tests known from the prior art are partially laborious in their performance and thus inappropriate for the routine field and high-throughput technologies.

The present invention has been based on the technical problem to provide means and methods which can be handled as easily as possible on the one hand and, moreover, allow serologic follow-up of the real degree of infection.

The present problem is solved by a carrier for diagnostics and/or follow-up of *Treponema* infection, which comprises at least one immobilized cardiolipin and at least one immobilized *Treponema*-specific antigen.

In a further preferred embodiment cardiolipin is used together with lecithin and cholesterol. In the following this combination of cardiolipin, lecithin und cholesterol will also be called VDRL antigen.

In a further preferred embodiment the VDRL antigen comprises the named components in the following mass ratios cardiolipin:lecithin:cholesterol with ratios of 0.1 to 4.0:1 to 5.0:1 to 10.0. In a further preferred embodiment the mass ratios are 1 to 3.0 for cardiolipin:1 to 3 for lecithin:5 to 10 for cholesterol.

In a further preferred embodiment the carrier comprises several positions with cardiolipin, at least two, preferably at least three, particularly preferably at least four positions, at which cardiolipin is present in different concentrations. These concentrations are preferably for the individual positions as follows: 0.10 to 1.00 mg/ml (position 1), 0.05 to 0.50 mg/ml (position 2), 0.02 to 0.2 mg/ml (position 3), 0.01 to 0.1. mg/ml (position 4).

In a further preferred embodiment the carrier comprises several positions with VDRL antigen, at least two, preferably at least three, particularly preferably at least four positions, at which the VDRL antigen is present in different concentrations.

In a further preferred embodiment the carrier comprises at least two, preferably at least three, particularly preferably at least four different *Treponema*-specific antigens, each antigen being immobilized in a different position on the carrier.

In a further preferred embodiment the *Treponema*-specific antigens are selected from antigens of *Treponema pallidum*, preferably 15 kD, 17 kD, 44.5 kD and 47 kD antigens.

In a further preferred embodiment the carrier comprises further controls suited to indicate the correct performance of the inventive method. For instance, among these controls is a serum control, preferably protein A. This control indicates that the test strip has actually been contacted with serum during performance of the method.

In a further preferred embodiment the control represents a so-called cut-off control, which for instance comprises a dilution of purified human immunoglobulin. This control serves evaluation purposes in that a weaker signal than the cut-off control corresponds to a negative test result whereas a stronger signal corresponds to a positive test result. Nitrocellulose, PVDF (polyvinylidene difluoride), nylon, cellulose acetate, polystyrene are suited as carrier materials, nitrocellulose being particularly preferred. It has been found that the use of nitrocellulose gives a particularly good signal-background ratio, especially for the VDRL signal.

In a further preferred embodiment controls represent so-called conjugate controls. These controls indicate that during performance the test strip has been contacted with the corresponding conjugate which is directed against human IgG or human IgM or human IgA, respectively.

In a further preferred embodiment the carrier is formed as a test strip, especially in a format which allows application in conventional immunodiagnostic methods.

In a further preferred embodiment the carrier is formed as a Western blot. The carrier contains the various reagents in an immobilized form.

The above-mentioned technical problem is also solved by a method for diagnostics and/or follow-up of a *Treponema* infection, which is characterized in that an above-mentioned carrier is contacted with a patient's sample and the presence of antibodies against a *Treponema* antigen and/or cardiolipin in the patient's sample is thus determined.

Preferably, the patient's sample is a blood, serum, liquor or synovial fluid sample taken from the patient to be examined. The workflow of the method corresponds to standard methods in the field of immunodiagnostics and is known to a person skilled in the art.

In a further preferred embodiment the carriers are (automatically) read and evaluated after test performance with the evaluation software ViraScan®. The carriers are densitometrically analyzed with ViraScan®. The intensities of VDRL-IgG and VDRL-IgM bands and the *Treponema*-specific antigen bands are compared with the intensity of the cut-off control bands, which are also situated on the carriers. This allows a quantitative determination of the antibody reactivities.

The above-mentioned technical problem is further solved by a test kit for the diagnosis of a *Treponema* infection and/or the follow-up of a *Treponema* infection, the test kit comprising an above-mentioned carrier as well as the other reagents for the performance of the diagnostic method as well as an instruction manual for performing the assay.

Both *Treponema pallidum*-specific antibodies against the 47 kD, the 44.5 kD, the 17 kD and the 15 kD protein and antibodies against the VDRL antigen (cardiolipin:lecithin:cholesterol), particularly cardiolipin, can be detected in one step with the new test method and carrier, respectively.

A more reliable, better automated and more significant syphilis diagnosis can be ensured by combining *Treponema pallidum*-specific antigens (47 kD, 44.5 kD, 17 kD, 15 kD proteins) with non-*Treponema pallidum* antigens (e.g. cardiolipin) in one test format.

Thus, after a screening test (TPPA, TPHA, TPLA, Tp Elisa) it is possible, within the scope of step diagnostics for syphilis diagnosis, to subsequently perform both the serologic confirmatory reaction and the analysis for determining the need for therapy and also the serologic follow-up with the inventive carrier and method, respectively.

In particular, the follow-up of a *Treponema* infection becomes reliable and easily feasible with the carrier of the present invention. The measurement signal obtained with the VDRL antigen is a reliable factor for the degree of *Treponema* infection. While the reactivity found in the patient's sample with the *Treponema* antigens is relatively independent of the degree of infection (i.e. the severity of infection), the VDRL signal supplies more significant values in this respect.

In the evaluation of the VDRL signals the intensities of the individual VDRL bands are compared with the intensity of the cut-off control band and are assessed with 0, 1 or 2 ViraBlot units, depending on whether the VDRL bands are weaker, equally strong or definitively stronger than the cut-off control band. The sum of the individual VDRL-ViraBlot units indicates the reactivity of the present lipoid antibodies. Here, the increasing sum of VDRL-ViraBlot units correlates with an increase in the reactivity of the lipoid antibodies. ViraBlot unit means that the value 1 is predetermined when a signal observed with a VDRL band shows the same intensity as the signal obtained with the cut-off control band. 0 means that the signal of the VDRL band is significantly weaker than the signal of the cut-off control band and the value 2 means that the intensity of the VDRL band is significantly higher than the intensity of the cut-off control band. The greater the number of determined ViraBlot units, the higher is the reactivity of antibodies, in the analysis sample, with the VDRL bands.

Finally, the carrier of the present invention and the method performed therewith allow a differentiation between the antibody classes IgG and IgM directed against VDRL. Particularly, this also offers advantages in diagnosis, e.g. in the assessment of the therapy need for children with moot congenital syphilis.

Surprisingly, it has particularly been possible to immobilize the body's own lipids (cardiolipin, lecithin and cholesterol) on a solid carrier such that their reactivity with the antibodies of the patient's material is maintained. This has certainly been unexpected because the lipid structures, particularly in the case of cardiolipin, are relatively unstable three-dimensional structures, so that application to a solid carrier represented a high risk of destroying the relevant epitopes. Surprisingly, the diagnostically relevant epitopes are maintained on the solid carrier even after fixation, thereby allowing a rapid, easy and, nevertheless, reliable detection of the antibodies directed against cardiolipin.

SHORT DESCRIPTION OF THE FIGURES

FIG. 5 shows IgG and IgM responses of the carrier of the present invention after reaction with human serum in a mother and her child with moot congenital Syphilis.

The following examples will illustrate the invention in more detail.

Figure 1:
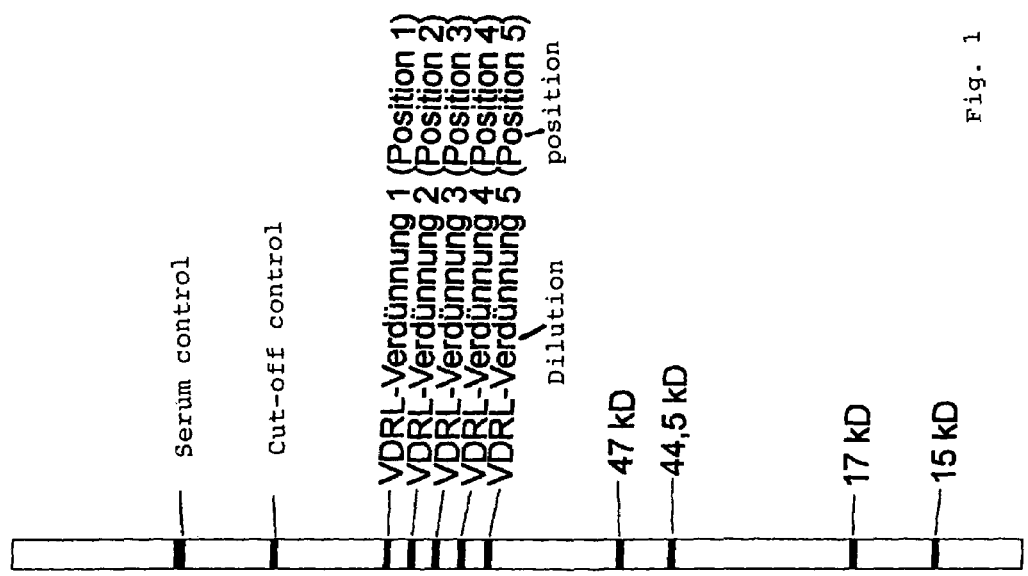
FIG. 1 shows a carrier of the present invention with VDRL antigens of different concentrations and with four different *Treponema pallidum* antigens, serum control and cut-off control.
Figure 2:
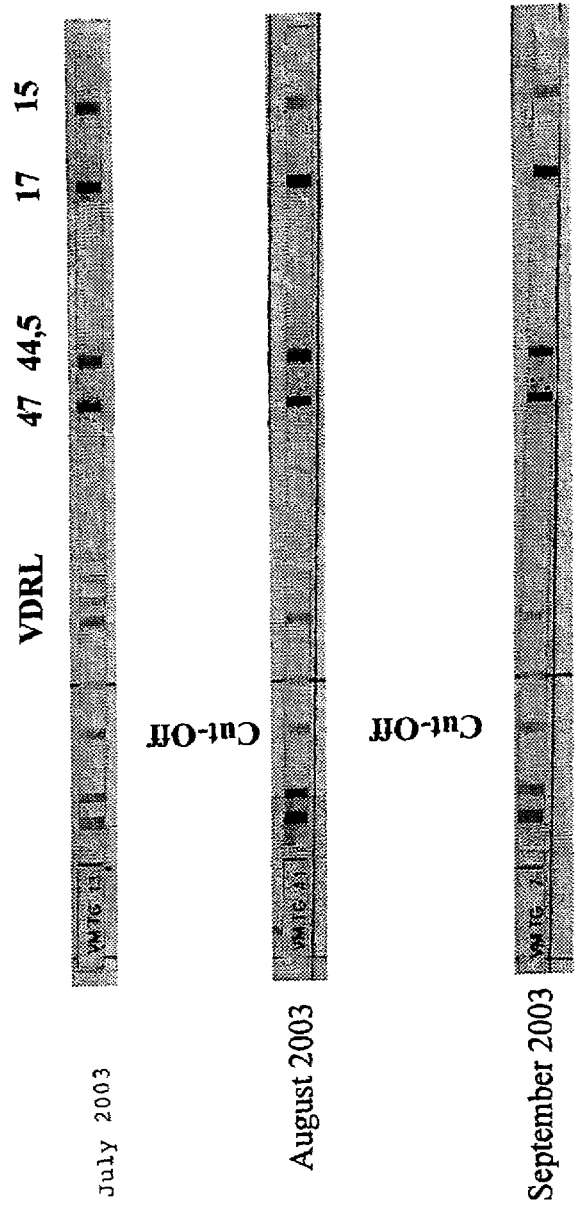
FIG. 2 shows a carrier of the present invention for the VDRL-IgG follow-up in a patient with Lues II.

FIG. 2 shows test strips of type IgG for the VDRL-antigen follow-up in a Lues II patient. The tests were performed within a period of three months at an interval of one month each. The *Treponema*-specific antigen bands are clearly visible in each test strip. The decrease in the VDRL-IgG titer in the course of subsiding infection after therapy is clearly visible on the VDRL-antigen bands.

The VDRL ViraBlot units correlate with the known, conventionally determined VDRL or cardiolipin CBR titers. In the following this correlation will be illustrated in FIG. 3.

Figure 4:
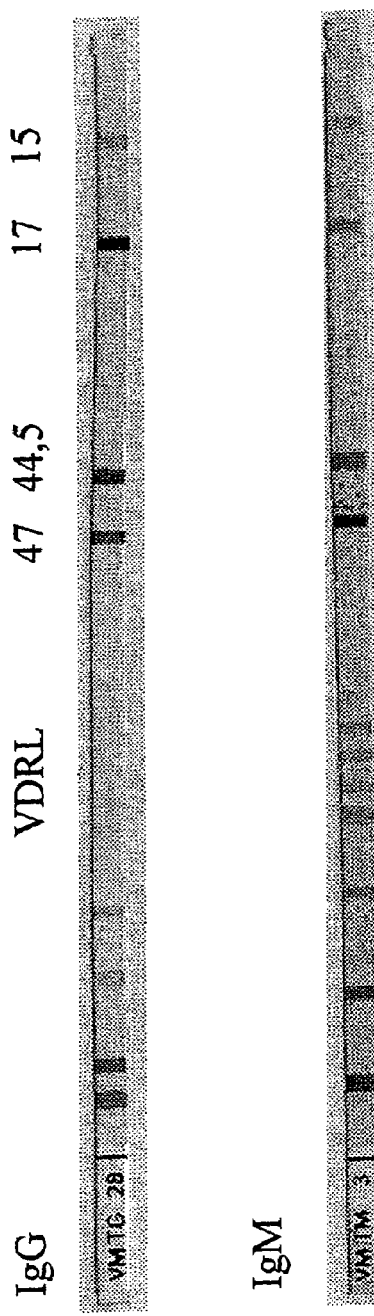
FIG. 4 shows IgG and IgM responses of the carrier of the present invention after reaction with human serum in a Lues II patient with HIV infection.

In FIG. 4 *Treponema*+VDRL ViraBlot IgG and IgM immune responses to Lues II in a HIV patient are illustrated. The bands of the *Treponema*-specific antigens 47 kD, 44.5 kD, 17 kD and 15 kD are each clearly visible in IgG and IgM. VDRL bands are only clearly visible in IgM and not in IgG.

In adding up the individual ViraBlot units for the VDRL-ViraBlot IgG and IgM antibody findings and evaluating the same with the *Treponema*-specific bands, one can see that the patient, depending on the course of the disease, either recently suffered from an infection or is still in an active syphilis stage. The application of the VDRL antigens and *Treponema*-specific antigens onto a carrier simplifies the test performance and allows a rapid serodiagnostic statement at a glance. Instead of performing two tests consecutively (e.g. VDRL and 19S-IgM-FTA-ABS), as has so far been the case, these are now integrated in one step.

In FIG. 5 the immunoreactivities of VDRL and *Treponema*-specific antigens in IgG and IgM immunoassay in a mother and her child with suspicion of congenital Syphilis is illustrated. The antigen bands 47 kD, 44.5 kD, 17 kD and 15 kD are each clearly visible in the IgG of the mother and the child and in the IgM of the mother.

The sum of the individual ViraBlot units for the VDRL-ViraBlot IgG and IgM antibody findings in the immune response of the mother indicates a distinct reaction for the lipoid antibodies. *Treponema*-specific IgG and IgM bands together with the VDRL-ViraBlot IgG and IgM antibody findings thus indicate that the mother recently suffered from a *Treponema* infection or, depending on the anamnesis, is still in an active infection stage.

Since IgM antibodies are normally not transferred across the placenta to the fetus the need for therapy would only exist if *Treponema*-specific IgM antibodies and/or IgM-VDRL antibodies pointed to an infection in the newborn, which is not the case in this example. Thus, in this case the detection of IgG antibodies in the child indicates that they have been transferred from the mother across the placenta.

In contrast to the conventional tests the present invention makes a distinction between anti-VDRL-IgG and anti-VDRL-IgM antibodies. This distinction allows a better statement on the need for therapy in a child with moot congenital syphilis.

According to the conventional test methods and the resultant outcome (TPPA, 19S-IGM-FTA-ABS, IgG-FTA-ABS and cardiolipin CBR) the child would have been in therapy in this example, in particular, because of the positive cardiolipin CBR value (1:40).

With the present invention, a negative test result is obtained in this example for both the IgM-VDRL antibodies and the *Treponema*-specific IgM antibodies, which does not point to the need for therapy for the child. This example supports the advantage of a separate detection of different antibody reactivities in the analytical material.

Preparation of the *Treponema* Test Strip

Preparation of the VDRL Antigen

VDRL antigen was prepared from a mixture of the individual components cardiolipin, lecithin and cholesterol in ethanol. Cardiolipin was purified from bovine heart (Avanti Polar Lipids Inc., Alabaster, AL, USA), lecithin from hen's egg (Avanti Polar Lipids Inc., Alabaster, Ala., USA) and cholesterol from wool grease (Avanti Polar Lipids Inc., Alabaster, Ala., USA). The individual components were used at purity levels of at least 98%. The individual components were present in each case as dry substance and were diluted in ethanol (100%). The concentration of cardiolipin was 4 g/l in ethanol (100%), the concentration of lecithin was 100 g/l in ethanol (100%), and the concentration of cholesterol was 25 g/l in ethanol (100%). In the order of cardiolipin, lecithin and cholesterol the individual components were mixed in the desired mixing ratio. The mixture is stored at room temperature for 12-24 hours in the dark before further processing. In the VDRL mixture the mass ratios of cardiolipin:lecithin:cholesterol were in the range of (0.1-4.0):(0.1-5.0):(0.1-10.0). Good results were obtained with a mixture of cardiolipin:lecithin:cholesterol with a mass ratio of 2.0:1.4:9.0.

Preparation of VDRL Dilutions

VDRL antigen was gradually prepared in 1.4 to 1000 times dilution in phosphate-buffered saline solution pH 7.2.

Preparation of *Treponema*-specific Antigen Solutions 47 kD protein from *Treponema pallidum* (Capricorn, USA), 44.5 kD protein from *Treponema pallidum* (Lee Laboratories, USA), 17 kD protein from *Treponema pallidum* (Lee Laboratories, USA) and 15 kD protein from *Treponema pallidum* (Lee Laboratories, USA) were used for the preparation of the *Treponema*-specific antigen solutions. The antigens were diluted in phosphate-buffered saline solution pH 7.2. Concentrations between 1 µg/ml and 200 µg/ml per antigen were used. Well suited for the 47 kD protein are solutions in a concentration of 60 µg/ml, for the 44.5 kD protein solutions in a concentration of 5 µg/ml, for the 17 kD protein solutions in a concentration of 10 µg/ml and for the 15 kD protein solutions in a concentration of 20 µg/ml.

Immobilization of the Antigens on Solid-phase Carrier Material

Nitrocellulose (Schleicher and Schüll, Dassel, Germany) was used as solid-phase carrier material. The correspondingly diluted antigens (concentrations: VDRL: 1.40 times, 28.6 times, 55.6 times and 111.1 times dilution of the VDRL antigen solution; 47 kD protein: 60 µg/ml; 44.5 kD protein: 5 µg/ml; 17 kD protein: 10 µg/ml; 15 kD protein: 20 µg/ml) could be bound to nitrocellulose as the solid-phase carrier material by passive adsorption. The antigen solutions were applied by an automatic dispenser at drop sizes of 10.67 nl to 85 nl and flow rates of 0.5 µl/cm to 5.0 µl/cm.

Blocking of Free Binding Sites

Nitrocellulose coated with antigen was incubated in a buffer of trishydroxymethylaminomethane (3.25 g/l), sodium chloride (7.51 g/l), TWEEN® 20 (polyoxyethylenesorbitan monolaurate) (3.83 ml/l), thimerosal (0.02 g/l), milk powder (40 g/l), pH 7.5, at 37.degree. C. for 30 mm, afterwards incubated and dried in a buffer of trishydroxymethylaminomethane (3.25 g/l), sodium chloride (7.51 g/l), TWEEN®

20 (polyoxyethylenesorbitan monolaurate) (3.83 ml/l), thimerosal (0.02 g/l), milk powder (5 g/l), pH 7.5, at 37.degree. C. for 30 mm.

The blocked nitrocellulose was cut into strips for further application (test strips).

Development of the Nitrocellulose Strips with Sample Material

Serum, plasma, CSF (cerebrospinal fluid) or synovial fluid are suitable as sample fluid.

The nitrocellulose strip coated with antigen (=test strip, for instance illustration 1) is incubated in 1.5 ml washing buffer consisting of trishydroxymethylaminomethane (3.25 g/l), sodium chloride (7.51 g/l), TWEEN® 20 (polyoxyethylenesorbitan monolaurate) (3.83 ml/l), thimerosal (0.02 g/l), milk powder (5 g/l), pH 7.5, at room temperature for 5 min on a platform rocker in a well. Afterwards the buffer is decanted. 20 µl sample fluid together with 1.5 ml wash buffer are added to the test strip. The test strip is incubated on the platform rocker for 30 min. After incubation with sample fluid the test strip is washed three times each with 1.5 ml wash buffer and subsequently incubated with anti-human-IgG or anti-human-IgM or anti-human-IgA alkaline phosphatase conjugate. Afterwards it is washed three times each with 1.5 ml wash buffer in each case for 5 min. In a further wash step it is re-washed with distilled water for 1 min and subsequently developed with chromogen/substrate solution (BCIP/NBT). The development is stopped according to the coloring of a cut-off control through decantation of the developing fluid and by washing three times each with 1.5 ml distilled water.

Interpretation of the Coloring on the Test Strips

Coloring intensities of the antigen lines are compared with the coloring intensities of the cut-off control on the test strips. The coloring intensity can be quantified by scanning (commercial color scanner; program ViraScan®, Viramed, Planegg, Germany) the developed test strips. From the readings of the coloring intensities ratios to the cut-off control are calculated (ratio). If the ratio is greater than or equal to one, a correspondingly colored antigen line is assessed to be positive. If the ratio is less than one but greater than or equal to 0.5, the corresponding antigen line is assessed as a limit value. If the ratio is less than 0.5, the corresponding antigen line is assessed to be negative.

One or more positive antigen lines of the proteins 47 kD, 44.5 kD, 17 kD or 15 kD point to the presence of corresponding antibodies in the respective sample analyzed.

Figure 3:
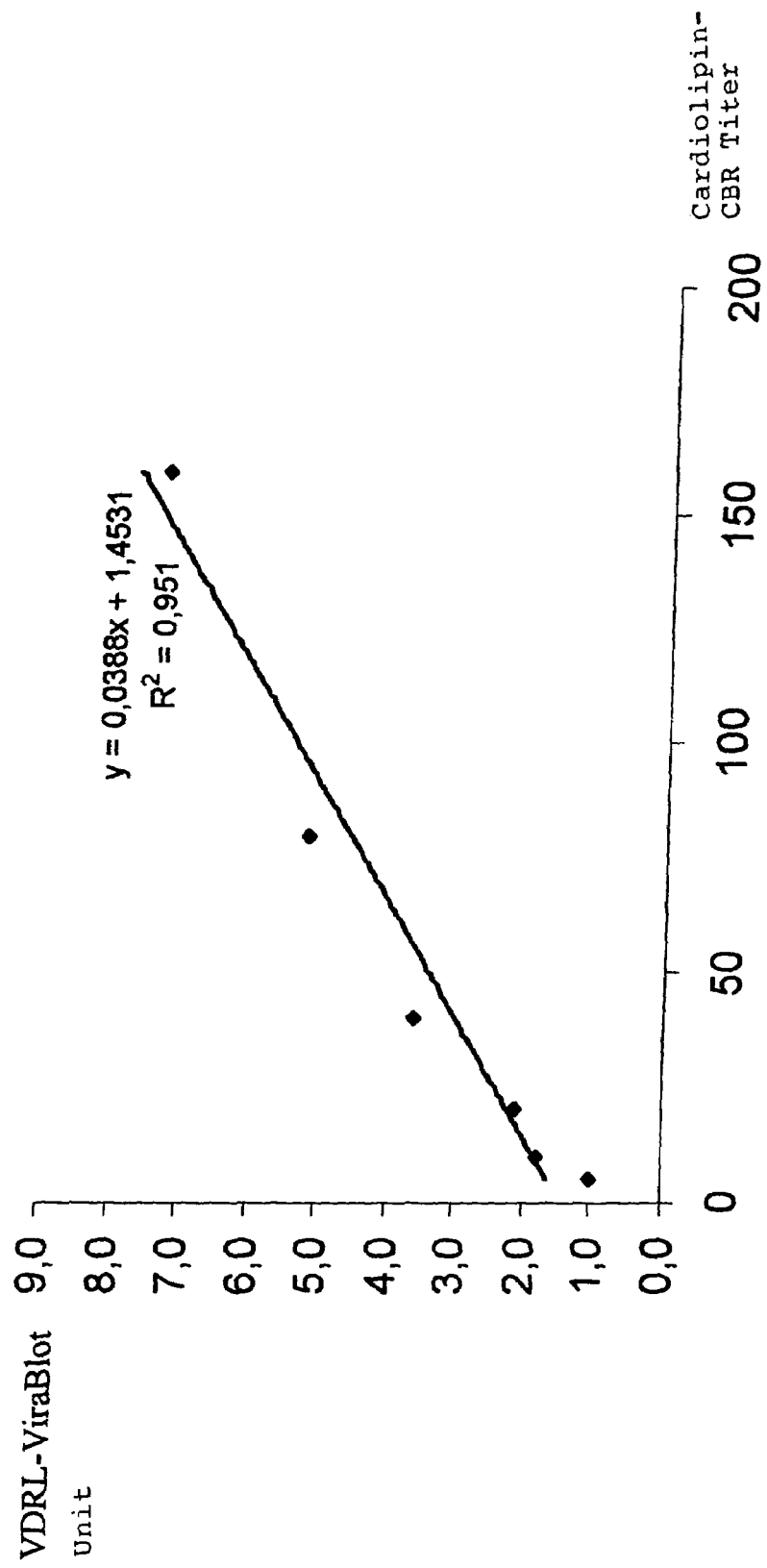
FIG. 3 shows the correlation of VDRL ViraBlot units with the known, conventionally determined VDRL or cardiolipin CBR titer.

One ore more positive antigen lines of the applied VDRL dilution levels point to the presence of anti-cardiolipin antibodies of a corresponding titer. There is a correlation between the VDRL titer, determined by conventional VDRL test method, and the quantifiable coloring intensity of the VDRL antigen lines on the test strip (FIG. 3). Thus, the carrier-bound VDRL is an appropriate means for the quantitative, at least semi-quantitative, detection of anti-cardiolipin antibodies and thus can be used for the follow-up of a *Treponema* infection.

The invention claimed is:

1. A carrier for diagnosis and/or follow-up of a *Treponema* infection, comprising
   a) at least one immobilized cardiolipin and
   b) at least one immobilized *Treponema*-specific antigen.

2. The carrier according to 1, characterized in that the cardiolipin is present together with lecithin and cholesterol as Venereal Disease Research Laboratory (VDRL) antigen.

3. The carrier according to claim 1, characterized in that the cardiolipin is present in at least two different concentrations at different positions of the carrier.

4. The carrier according to claim 1, characterized in that at least two different *Treponema* antigens are present in different positions on the carrier.

5. The carrier according to claim 1, characterized in that the at least one *Treponema*-specific antigen is selected from *Treponema pallidum*-specific antigens.

6. The carrier according to claim 1, characterized in that the carrier further comprises controls.

7. The carrier according to claim 1, characterized in that the carrier comprises a serum control.

8. The carrier according to claim 1, characterized in that the carrier comprises a cut-off control.

9. The carrier according to claim 1, characterized in that the carrier comprises a serum control and a cut-off control.

10. The carrier according to claim 1, characterized in that the carrier comprises a material selected from the group consisting of nitrocellulose, PVDF (polyvinylidene difluoride), nylon, cellulose acetate, and polystyrene, wherein the at least one immobilized cardiolipin and at least one immobilized *Treponema*- specific antigen are immobilized on the material.

11. The carrier according to claim 1, characterized in that the carrier is a test strip for use in immunodiagnostics.

12. The carrier according to claim 1, characterized in that the carrier is an immunoblot.

13. The carrier according to claim 2, characterized in that the VDRL antigen is present at different positions on the carrier such that anti-VDRL-IgG and anti-VDRL-IgM antibodies can be differentiated after reaction with a patient's sample.

14. A method for diagnosis and/or follow-up of a *Treponema* infection comprising:
   contacting a carrier according to claim 1 with a patient's sample and
   determining the presence of antibodies against a *Treponema* antigen and/or a cardiolipin on the test strip.

15. The method according to claim 14, comprising determining the reactivity of antibodies from a patient's serum with the cardiolipin of the test strip several times over a prolonged period of time.

16. The method according to claim 14, characterized in that the patient's sample is blood, serum, plasma, liquor or synovial fluid.

17. The method according to claim 14, further comprising differentiating anti-VDRL-IgG and anti-VDRL-IgM antibodies in a patient's sample.

18. A test kit for the diagnosis of a *Treponema* infection and/or the follow-up of a *Treponema* infection, comprising a carrier according to claim 1 and further reagents as well as an instruction manual for using the carrier.

19. A method of diagnosing or following-up a *Treponema* infection in a patient comprising:
   contacting a sample from a patient with a carrier according to claim 1 and
   measuring antibodies from the sample bound to the carrier.

20. The carrier according to 1, characterized in that cardiolipin, lecithin, and cholesterol are present in a cardiolipin:lecithin:cholesterol mass ratio of 0.1-4.0:1-5.0:1-10.

21. The carrier according to claim 3, wherein the cardiolipin is present in at least three different concentrations, at different positions of the carrier.

22. The carrier according to claim 3, wherein the cardiolipin is present in at least four different concentrations, at different positions of the carrier.

23. The carrier according to claim 4, wherein at least three different *Treponema* antigens are present in different positions on the carrier.

24. The carrier according to claim 4, wherein at least four different *Treponema* antigens are present in different positions on the carrier.

25. The carrier according to claim 5, wherein the at least one *Treponema pallidum* -specific antigen is selected from the group consisting of the 15 kD, 17 kD, 44.5 kD and 47 kD antigens.

26. The carrier according to claim 7, wherein the serum control comprises protein A.

27. The carrier according to claim 8, wherein the cut-off control comprises purified human immunoglobulin.

28. The carrier according to claim 9, wherein the serum control comprises protein A, and the cut-off control comprises human immunoglobulin.

29. The carrier according to claim 13, wherein the patient's sample is selected from the group consisting of blood, serum, plasma, liquor, and synovial fluid.

30. The carrier according to claim 10, characterized in that the carrier comprises nitrocellulose.

31. A test strip for diagnosis and/or follow-up of a *Treponema* infection, wherein the test strip comprises cardiolipin and at least one *Treponema*-specific antigen immobilized on the test strip to permit binding of an antibody specific for cardiolipin and an antibody specific for the *Treponema*-specific antigen(s).

32. The test strip of claim 31, wherein cardiolipin is present together with lecithin and cholesterol as Venereal Disease Research Laboratory (VDRL) antigen.

33. The test strip of claim 32, wherein the VDRL antigen and at least one *Treponema*-specific antigen are immobilized at multiple positions on the test strip.

34. The test strip of claim 33, wherein the test strip comprises nitrocellulose.

* * * * *